United States Patent [19]

Miyake et al.

[11] Patent Number: 4,812,392

[45] Date of Patent: Mar. 14, 1989

[54] METHOD AND APPARATUS FOR INCUBATING CELLS

[75] Inventors: Shinichi Miyake; Shinji Miyasaka, both of Osaka, Japan

[73] Assignee: Sumitomo Electric Industries, Ltd., Osaka, Japan

[21] Appl. No.: 814,246

[22] Filed: Dec. 27, 1985

[30] Foreign Application Priority Data

Dec. 27, 1984 [JP] Japan .............................. 59-278996
Dec. 27, 1984 [JP] Japan .............................. 59-280893

[51] Int. Cl.$^4$ ........................... C12Q 3/00; C12M 1/36
[52] U.S. Cl. ........................................ 435/3; 435/289; 435/243; 422/65; 436/163
[58] Field of Search ................... 435/3, 253, 289, 284; 422/73, 65; 436/163

[56] References Cited

U.S. PATENT DOCUMENTS

| | | |
|---|---|---|
| 2,975,553 | 3/1961 | Paul ..................................... 435/289 |
| 4,033,825 | 7/1977 | Haddad et al. ......................... 435/3 |
| 4,154,652 | 5/1979 | Sawamura et al. ..................... 435/3 |
| 4,481,296 | 11/1984 | Halley ................................. 436/163 |
| 4,676,951 | 6/1987 | Armes et al. .......................... 422/73 |
| 4,720,463 | 1/1988 | Farber et al. .......................... 422/65 |
| 4,727,033 | 2/1988 | Hijikata et al. ....................... 422/65 |

FOREIGN PATENT DOCUMENTS 58-105065 6/1983 Japan ..................................... 422/65

Primary Examiner—Benoit Castel
Attorney, Agent, or Firm—Cushman, Darby & Cushman

[57] ABSTRACT

A method and apparatus for the continued incubation of cells in a liquid culture medium. When the pH value of the culture medium deviates during the incubation from a pH range suited for the growth or multiplication of the cells, the culture medium is automatically replaced. Whether or not the pH value of the culture medium has deviated from the acceptable pH range is determined by measuring the intensity of light absorbed by the culture medium.

2 Claims, 4 Drawing Sheets

METHOD AND APPARATUS FOR INCUBATING CELLS

BACKGROUND OF THE INVENTION

The present invention generally relates to the incubation of living cells and, more particularly, to a method and apparatus for the continued incubation of the cells in a liquid culture medium.

Incubation of cells in a liquid culture medium containing various nutrients has long been practiced. The cells in the culture medium consume the nutrients for the multiplication or the growth thereof, and the pH value of the culture medium naturally varies with progressive consumption of the nutrients and metabolism of the cells. When the nutrients are consumed to less than a certain concentration, or when the pH value of the culture medium varies to such an extent as to deviate from a pH range suited or required for the growth of the cells, the cells will no longer be active to increase, i.e., multiplicate or grow. Once such a condition has arisen, the continued, positive incubation of the cells is possible provided that the liquid culture medium in which the cells have been placed is replaced with a fresh one of the same composition.

Hitherto, the time at which the liquid culture medium should be replaced is determined by monitoring the liquid culture medium to see if the color of a pH indicator such as, for example, Phenol red, contained in the culture medium has changed as a result of the change in pH value. Once the time has been determined, a tray carrying the culture medium to be replaced is transported to a sterile room where the replacement takes place subsequently. During the transportation and the subsequent replacement, human labors intervene frequently, thereby posing such a problem that the culture medium may be often contaminated with foreign germs.

In any event, according to the conventionally practiced method, the determination of the pH value of the culture medium based on the change in color of the pH indicator does not necessarily bring about an accurate measurement, and it happens very often that the composition of the culture medium remains in a range unsuitable for incubation of the cells, or the culture medium is left for a long time under conditions unsuitable for incubation of the cell. In the worst case, the cells will be killed.

The killing of the cells may occur even when the culture medium has been contaminated with foreign germs as discussed above. This is because the pH value of the liquid culture medium may change with either metabolism of the contaminant germs or extraordinary multiplication of the contaminant germs.

SUMMARY OF THE INVENTION

The present invention has been developed with a view to substantially eliminating the above described disadvantages and inconveniences inherent in the prior art method and has for its object to provide a method for the continued incubation of cells in a liquid culture medium with no intervention of human labors required.

It is a related object of the present invention to provide an automatic apparatus capable of performing the above mentioned method of the present invention.

According to one aspect of the present invention, there is provided a method for incubating cells in which the monitoring of a culture medium as to its pH value is carried out by irradiating a transparent vessel, such as, for example, a microplate, a dish or a glass bottle, containing cells to be incubated in a liquid culture medium, with visible light to produce a spectrum of light reflected from or transmitted through the culture medium, and then calculating the pH value of the culture medium from the spectrum of light so produced.

In the practice of the method of the present invention, the liquid culture medium contains not only the cells to be incubated and nutrients necessary for the multiplication of the cells, but also a low concentration of Phenol red sufficient to avoid any harm to the cells. So far as Phenol red is employed in a very low concentration, the pH indicator has absorption peaks at about 430 to 440 nm and 560 nm and an isosbestic point at 480 nm. In a pH range of 6.8 to 7.6 suitable for the cell growth, the absorption peak at about 430 to 440 nm increases with decrease of the pH value whereas that at about 560 nm decreases with decrease of the pH value. When ratios of the absorption intensity of the peak at about 430 to 440 nm and that at about 560 nm are plotted, the points plotted altogether lie on or substantially in a single continuous curve (See FIG. 9 of the accompanying drawings) from which a particular pH value can be determined against the ratio of these absorption peaks.

In practice, the light used to irradiate the transparent vessel containing the liquid culture medium with the cells may, when the wall of the vessel is contaminated, be unnecessarily absorbed or scattered by the contaminant. Similarly, the irradiating light may be unnecessarily absorbed or scattered by the cells being incubated within the transparent vessel. Therefore, the result of the spectral measurement includes a portion caused by such absorption and/or scattering. For accurate calculation of the pH value, the difference between the absorption intensity at about 430 to 440 nm or about 560 nm and that at a wavelength at which Phenol red does not exhibit absorption, for example, at 650 nm, should be used in the determination of a particular ratio determinative of the pH value.

It is to be noted that, depending on the kind and quantity of one or more of the nutrients used in the culture medium, correction may be required of the conversion curve shown in FIG. 9.

Once the pH value of the culture medium has been determined not suited for the growth of the cell, i.e., deviating from a predetermined pH range, the culture medium is automatically replaced with a fresh medium for the continued incubation of the cells. Thus, the method and the apparatus according to the present invention are effective to substantially free attendant researchers from timeconsuming, complicated and uneconomical manipulation jobs that have been hitherto required.

BRIEF DESCRIPTION OF THE DRAWINGS

These and other objects of the present invention will become readily understood from the following description taken in conjunction with a preferred embodiment thereof with reference to the accompanying drawings, in which.

DETAILED DESCRIPTION OF THE EMBODIMENT

Figure 6:
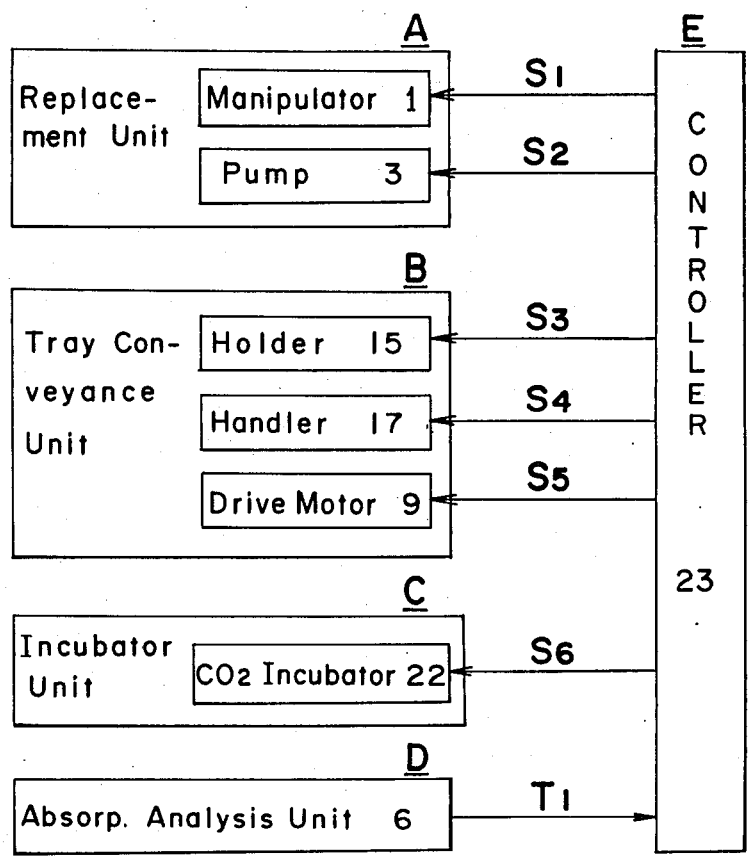
FIG. 6 is a block diagram of the incubator system.

Referring to FIG. 6, an incubating system according to the present invention generally comprises a replacement unit A, a tray conveyance unit B, an incubator unit C, an absorption analysis unit D and a control unit E. The control unit E employs a computer programmed to control the sequence of operation of the units A to D and supplies control signals $S_1$ and $S_2$ to the replacement unit A for controlling the operation of a manipulator and a pump, respectively, both of said manipulator and said pump constituting respective parts of the replacement unit A. The control signal $S_1$ is determinative of the sequence of operation of the manipulator, the direction of movement of the manipulator and other duties, whereas the control signal $S_2$ is determinative of the quantity of liquid to be sucked, the quantity of liquid to be discharged, the timing at which the liquid is to be sucked, the timing at which the liquid is to be discharged, and other duties.

The control unit E also supplies signals $S_3$, $S_4$ and $S_5$ to the tray conveyance unit B for controlling the sequence of operation of a stepper motor and a tray holder, respectively, (for example, the position of a tray support, the sequence of conveyance, the sequence of operation of the tray holder, and others), both of said stepper motor and said tray holder constituting respective parts of the tray conveyance unit B.

Moreover, the control unit E supplies a control signal $S_6$ to the incubator unit C for controlling incubating conditions (including, for example, temperature, incubating time, quantity of $CO_2$ and others). The absorption analysis unit D applies a measurement signal $T_1$ to the control unit E.

All of the units constituting the incubating apparatus are enclosed or placed in a sterile chamberdefining structure through which sterilized air is circulated at all times during the incubation.

More specifically, referring to FIGS. 1 to 8, a tray 7 containing a liquid culture medium and cells to be incubated is placed on a tray support 14. The control unit E subsequently generates a signal (through a signal line $S_3$), and in response thereto the tray holder 15 having a pair of pivotally connected holder arms is activated to cause the holder arms to hold the tray 7 from opposite lateral directions.

Figure 4:
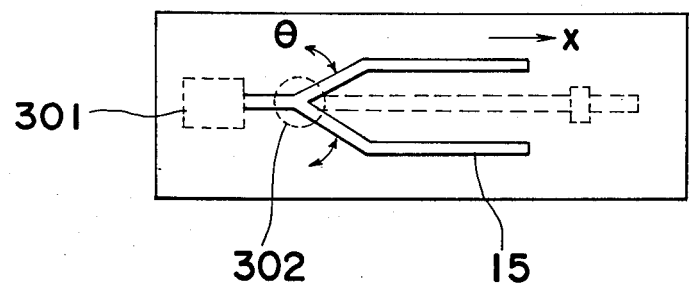
FIG. 4 is a schematic top plan view showing a tray holder.
Figure 5:
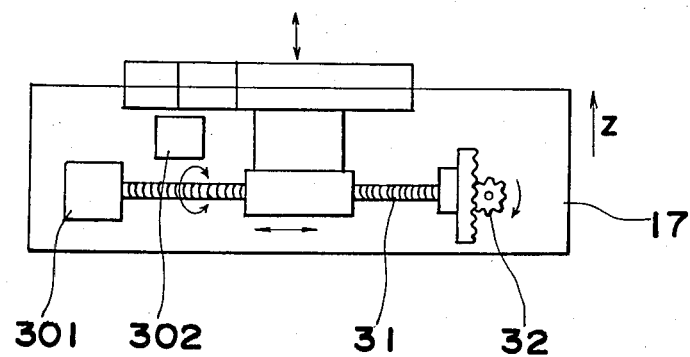
FIG. 5 is a schematic side view showing a drive system for the tray holder.

The holding of the tray 7 by the tray holder 15 is carried out by a motor drive system as best shown in FIGS. 4 and 5. Referring to these figures, when an electric motor 301 is operated in response to the signal $S_1$, a screw shaft 31 forming a part of a ball-screw assembly is rotated to move the tray holder 15 in one of the opposite directions depending on the direction of rotation of the screw shaft 31. An electric motor 302 serves to move the holder arms of the tray holder 15 between release and hold positions in respective directions shown by $\theta$, and when the holder arms are moved to the hold position, the tray 7 can be held by the holder arms of the tray holder 15. The movement of the tray holder 15 in one of the up and down directions Z for bringing the tray holder above and beneath the tray support 14 is carried out by a rack-and-pinion arrangement 32, the pinion gear being coupled with an electric motor (not shown).

The above described sequential movement of the tray holder 15, though having been described as performed by the use of the electric motors, may be accomplished by the use of one or more pneumatically operated cylinders.

Figure 1:
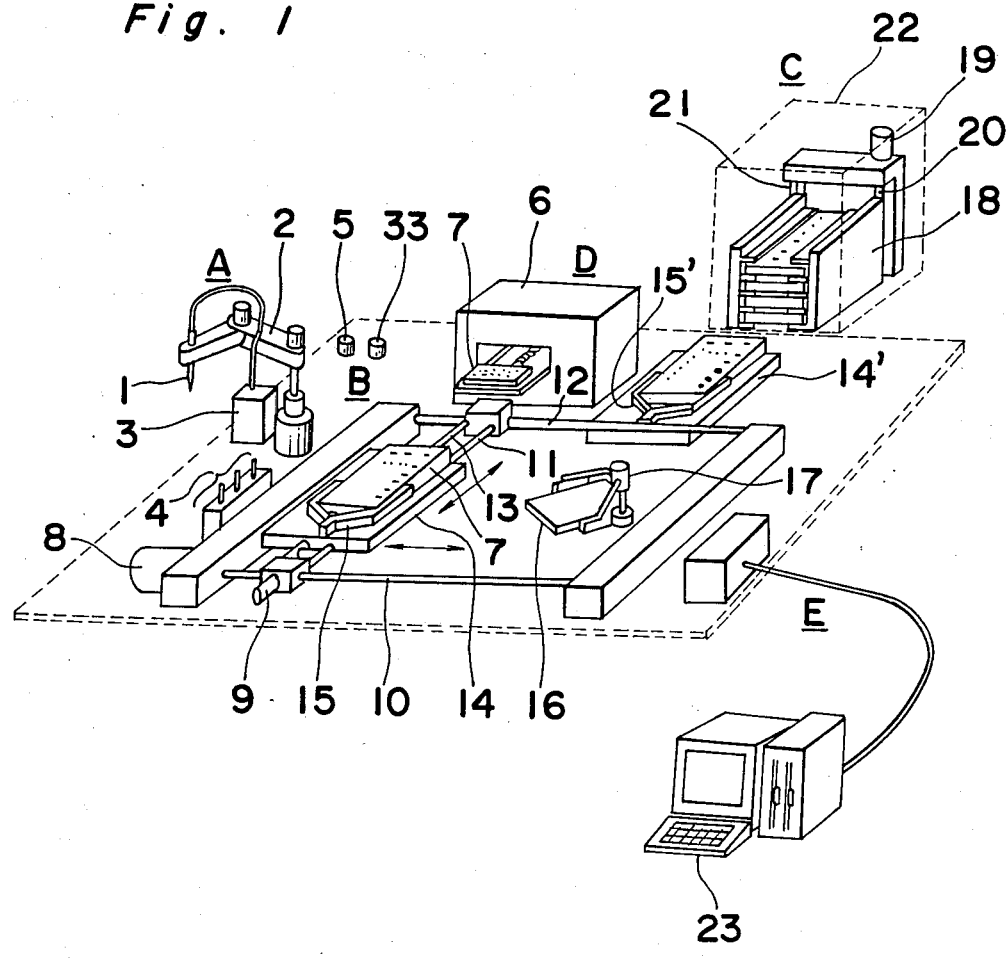
FIG. 1 is a schematic perspective view of an incubator system embodiment the present invention.

The tray 7 placed on the tray support 14 is transported to a $CO_2$ incubator 21, constituting a part of the incubator unit E, for the storage in a tray stock 18. For this purpose, the tray support 14 constituting a part of the tray conveyance unit B is moved from a first position as shown in FIG. 1 to a second position at which the tray support 14 is held in line with a tray support 14' located at the incubator unit C. This movement of the tray support 14 may be effected by the use of either an electric motor 25 as shown in FIG. 2 or a pneumatically operated cylinder 26 as shown in FIG. 3.

Figure 2:
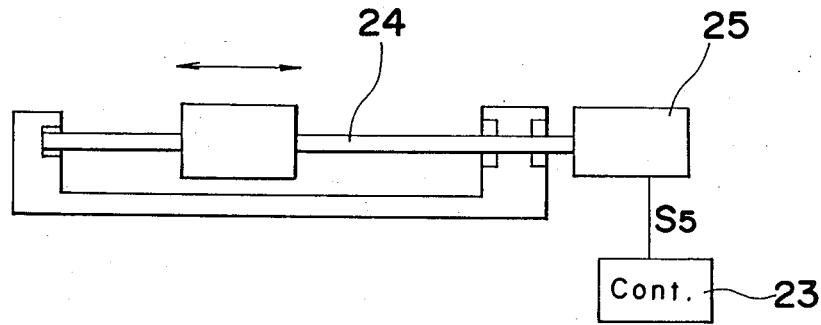
FIG. 2 is a schematic diagram showing a motor-driven model of a tray conveyance unit.
Figure 3:
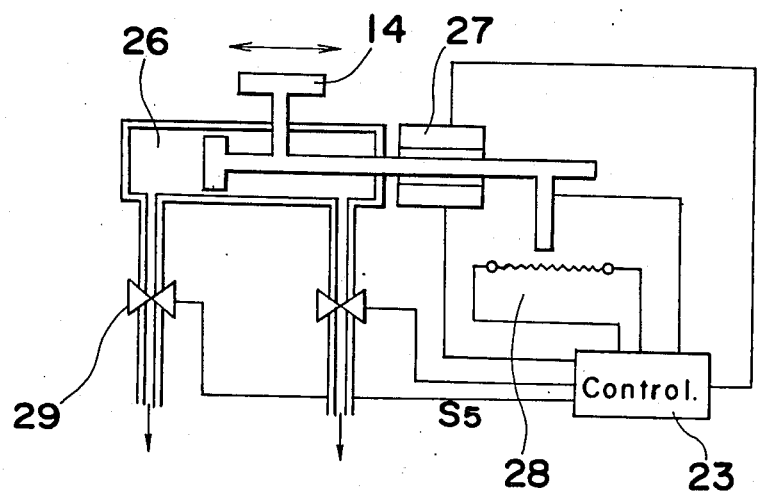
FIG. 3 is a schematic diagram showing a pneumatically driven model of a tray conveyance unit.

Referring to FIG. 2, the motor 25 employed is in the form of a stepper motor operable in response to the control signal $S_5$, generated from a controller 23, to drive a screw shaft 24 forming a part of a ball-and-screw assembly. Depending on the direction of rotation of the screw shaft 24, the tray support 14 is moved in one of the opposite directions as shown by the arrow.

Where the pneumatically operated cylinder 26 is employed as shown in FIG. 3. an electromagnetic valve 24 is controlled in response to the control signal $S_5$ to vary the air pressure inside the cylinder 26 for driving a piston of the cylinder 26. The movement of the piston brings about the movement of the tray support 14. The distance over which the piston has moved is detected by a potentiometer 28, and when the piston has moved a predetermined distance, an electromagnetic brake is activated in response to a signal from the controller 23 to bring the tray support to a halt.

By employing a pair of the mechanisms shown in FIG. 2 or FIG. 3 and arranging them in perpendicular relationship with each other, an X-Y tray conveyance mechanism capable of moving the tray support 14 in two directions perpendicular to each other can be fabricated.

Alternatively, the tray support may be driven by a generally endless cable having a portion rigidly connected to the tray support and trained between drive and driven pulleys.

Where the tray support 14 is positioned adjacent the tray support 14' and the tray 7 is placed thereon while the tray support 14 is so positioned, the tray support 14 in the tray conveyance unit B need not be always moved.

Referring back to FIG. 1, the tray 7 on the tray support 14 then moved to the second position adjacent the tray support 14' is transferred by the tray holder 15, activated in response to the signal $S_1$, in a direction X as shown in FIG. 4, onto the tray support 14'. When the tray 7 has been brought above the tray support 14', the tray holder 15 releases it to allow it to be placed on the tray support 14', followed by the activation of a tray holder 15', similar to the tray holder 15, to hold the tray 7 so transferred. Subsequent thereto, the tray holder 15' while holding the tray 7 moves in the direction X to insert the tray 7 into one of the racks of the tray stock 18. When the tray holder 15' is retracted from the tray stock 18 after having released the tray 7, the tray 7 is accommodated within the $CO_2$ incubator 21. The $CO_2$ incubator 21 has a conventionally well-known door assembly 22 as shown by the phantom line in FIG. 1, which door assembly 22 is selectively closed and opened at the time the tray 7 is accommodated into or removed from the incubator 21. The tray stock 18 comprises a shelf assembly, a screw feeder 20 for moving the shelf assembly up and down, and an electric drive motor 19 for driving the screw feeder 20.

Within the $CO_2$ incubator 21 having the tray stock 18 built therein, the cells in the culture medium within the tray 7 are incubated for a required period of time.

The replacement of the liquid culture medium during the incubation is performed in the following manner.

The tray 7 accommodated within the $CO_2$ incubator 21 is removed from the tray stock 18 and transferred onto the tray support 14 in a manner substantially reverse to that described hereinbefore. The tray support 14 carrying the tray 7 is then moved to a position adjacent an absorption analyzer 6 and is subsequently transferred into the analyzer 6 in a manner similar to the transfer of the tray 7 into the $CO_2$ incubator 21.

Within the absorption analyzer 6, the absorbence of the culture medium in each well of the tray 7 is measured. By way of example, where the controller 23 is required to calculate the pH value of the culture medium on the basis of the culture medium, at 430 nm and 560 nm, respectively, the absorbence of Phenol red at, for example, 650 nm at which Phenol red does not absorb light is first measured for the purpose of removing the absorption of light by the tray itself as well as that by the cells and is then subtracted from the absorbence at 430 nm and 560 nm so that the ratio can be given by the differences therebetween.

The tray 7 is, after the measurement, again transferred onto the tray support 14 in a manner substantially reverse to the loading thereof into the analyzer 6 and is then, if the pH measurement has indicated that the pH value measured was in a range suitable for the cell growth, accommodated into the incubator 21 in response to the signals $S_3$ and $S_5$ for the continued incubation.

The controller 23 determines if information conveyed by a measurement signal $T_1$ corresponds to a pH value falling within the acceptable pH range. Where the pH value of the culture medium in one or some of the wells in the tray 7 has been found deviating from the acceptable pH range, the replacement of the culture medium is carried out. For this purpose, the tray 7 on the tray support 7 is transported to a position adjacent a handler 17 (signal lines $S_3$ and $S_5$). The handler 17 is capable of being moved up and down and also selectively closed and opened by an electric motor drive system or a pneumatic drive system and grips a lid 16, which has been placed on the tray 7 for lifting (signal line $S_4$).

The tray 7 with the lid 16 removed by the handler 17 is then moved to a position adjacent a pipette manipulator 2 (signal line $S_5$). The pipette manipulator 2 has a pipette 1 fitted thereto, which pipette 1 can be moved to one of the wells, containing the culture medium to be replaced, by the movement of the manipulator 2 or the tray support 14 (signal line $S_1$ or $S_5$). The pipette 3 is then inserted into the well by the manipulator 2, and the culture medium to be replaced is pumped out of the associated well by a pump 3 (signal line $S_3$). At this time, the depth into which the pipette 1 is inserted is controlled to avoid any possible sucking of the cells. The culture medium sucked into the pipette 1 is transported by the pipette manipulator 2 to a recovery bin 33 (signal line $S_1$) and is then discharged by the pump 3 (signal line $S_2$). Thereafter, the pipette 1 is moved by the manipulator 2 to a pipette tip replacement station 4 at which the tip of the pipette 1 is replaced (signal line $S_1$). The replacement of the pipette tip is for the purpose of avoiding any possible contamination of a substitute culture medium. Instead of the replacement, the pipette tip may be washed. In any event, where there is no problem of contamination, the replacement of the pipette tip of the washing thereof may be omitted.

The pipette 1 having a new pipette tip fitted thereto at the replacement station 4 is moved by the manipulator 2 to a container 5 containing a substantial amount of culture medium (signal line $S_1$) with the culture medium subsequently sucked into the pipette by the pump 3 (signal line $S_2$). The culture medium so sucked into the pipette 1 is then moved by the manipulator 2 back to the well in the tray 7 and is injected by the pump 3 into such well (signal lines $S_1$ and $S_2$), thereby completing the replacement of the culture medium.

Figure 7:
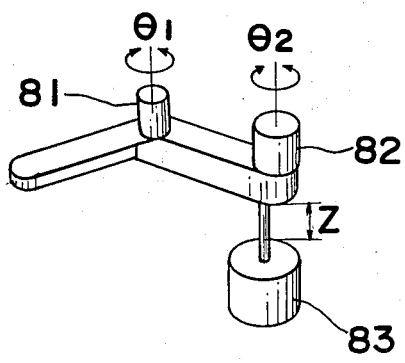
FIG. 7 is a perspective view of a manipulator used in the apparatus.

The pipette manipulator 2 is of any known construction, the details of an example of which is shown in FIG. 7. In FIG. 7, reference numerals 81 and 82 represent electric motors capable of imparting rotation about axes $\theta_1$ and $\theta_2$. The manipulator 2 has a leg portion 83 in which an electric motor and a rack-and-pinion arrangement are accommodated for moving the manipulator 2 as a whole in one of the opposite directions Z. The control of these is carried out by the controller 23.

When the motor in the leg portion 83 of the manipulator 2 is rotated to lower the pipette manipulator with the pipette 1 consequently inserted into the well containing the culture medium to be replaced, the pump 3 is operated to suck the culture medium into the pipette 1. The amount of the culture medium to be sucked can be controlled by the controller 23 controlling the time during which the pump 3 is operated. Thereafter, the motors 81 and 82 are driven to control the manipulator 2 to move the pipette 1 to the well in the tray 7 and a predetermined amount of culture medium is then injected into the well. The injection of the culture medium into the well is possible by rotating the pump 3 is a direction reverse to that during the suction of the culture medium to be replaced, and the quantity of the culture medium to be injected can be controlled by controlling the time during which the pump 3 is rotated.

The above described procedure is repeated subject to some of the wells in the tray which contain the respective culture mediums all having a pH value deviating from the acceptable pH range. After the completion of the replacement of the culture medium, the tray 7 is, in a manner substantially reverse to the transportation thereof from the incubator 21 to the manipulator 2 (signal line $S_5$), moved to the handler 17 at which the lid 16 is mounted on the tray (signal line $S_4$), and then loaded into the tray stock 18 in the $CO_2$ incubator 21.

Hereinafter, the present invention will be described by way of an example which is set forth only for the purpose of illustration thereof.

EXAMPLE

Figure 9:
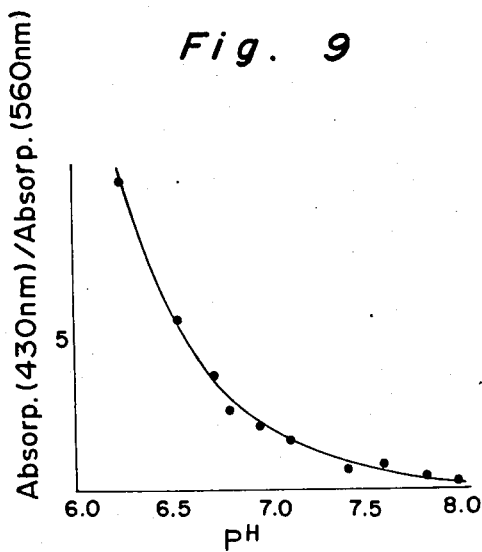
FIG. 9 is a graph showing a change of the ratio between the absorption peaks exhibited by Phenol red with change in pH value of the culture medium.
Figure 8:
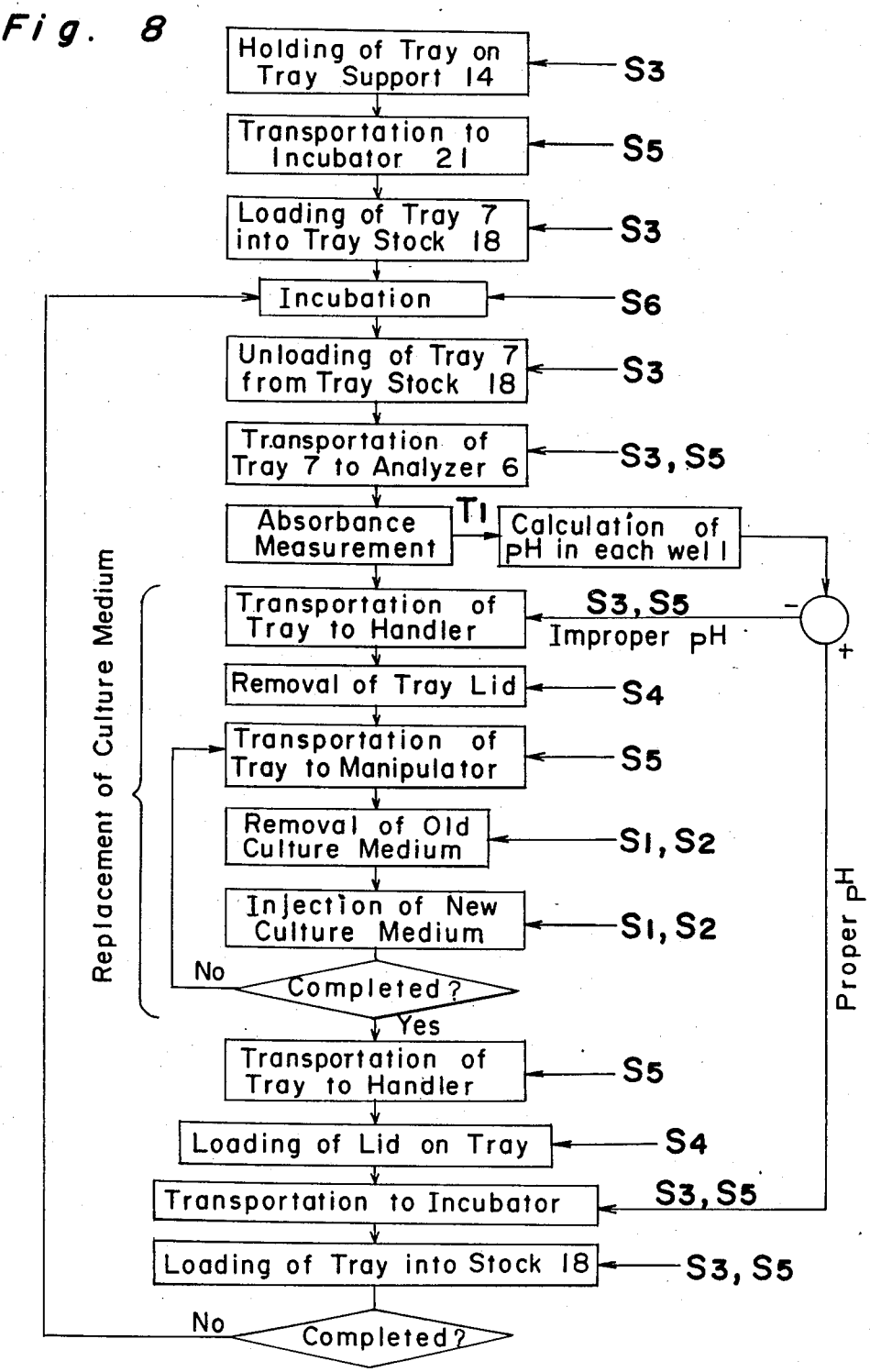
FIG. 8 is a flowchart showing the sequence of operation of the system.

On a microplate having 96 wells, mouse myeloma cells were incubated in a Dulbeccom MEM medium containing 14 mg/l of Phenol red (pH 6.8) in a $CO_2$ incubator for 2 days. Light absorption was measured by a photometer for microplate to find that the absorption intensities were 0.69 at 440 nm, 0.18 at 560 nm and 0.04 at 650 nm. Thus, the ratio of the absorption intensities at 440 nm and 560 nm was calculated to be 4.64 [=(0.69−0.04)/(0.18−0.04)]. This ratio corresponds to pH of 6.58 from FIG. 9, which was consistent with the actual pH value of 6.61 measured by a pH sensor. Since this pH value was not suitable for cell multiplication, the medium was changed. The incubation was continued for two weeks with measuring the pH value every two days. The cells multiplied well.

Although the present invention has been described in connection with the preferred embodiment thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for incubating cells in a liquid culture medium contained in a transparent vessel, which comprises the steps of: calculating the pH value of the culture medium containing cells to be incubated, from the ratio between the absorbencies of Phenol Red added to the culture, at two wavelengths of the absorption peak wherefrom the absorbance at a wavelength at which Phenol Red does not absorb is subtracted to account for the absorption of light by the cells, and, in the event that the pH value so calculated deviates from a predetermined pH range, replacing the culture medium with a fresh culture medium of identical composition, all of said steps being carried out while said cells are maintained in a steady state within said transparent vessel.

2. An incubating apparatus which comprises a replacement unit, a tray conveyor unit, an incubating unit an absorption analysis unit and a controller, said replacement unit comprising a pipette, a manipulator for carrying the pipette and a pump for causing the pipette to selectively suck up and discharge a quantity of liquid culture medium; said tray conveyor unit comprising a tray support for the support thereon of a tray and a drive means for transporting the tray support to positions adjacent the replacement, incubating and analysis units; said incubating unit comprising a tray stock for accommodating a plurality of trays; said controller being used to control all of the units.

* * * * *